United States Patent
Pendergrass

(10) Patent No.: US 7,249,490 B2
(45) Date of Patent: Jul. 31, 2007

(54) ISOLATED GAS SENSOR CONFIGURATION

(75) Inventor: Robert Pendergrass, Saugus, CA (US)

(73) Assignee: H2scan, LLC, Valencia, CA (US)

( * ) Notice: Subject to any disclaimer, the term of this patent is extended or adjusted under 35 U.S.C. 154(b) by 0 days.

(21) Appl. No.: 11/046,397

(22) Filed: Jan. 27, 2005

(65) Prior Publication Data
US 2005/0183968 A1 Aug. 25, 2005

Related U.S. Application Data

(60) Provisional application No. 60/540,018, filed on Jan. 27, 2004.

(51) Int. Cl.
*G01N 27/26* (2006.01)
(52) U.S. Cl. .............. 73/31.05; 73/23.2; 73/23.31; 73/31.01; 73/31.02; 73/31.03
(58) Field of Classification Search ............ 73/23.2, 73/23.31, 31.01, 31.02, 31.03, 31.05, 31.06
See application file for complete search history.

(56) References Cited

U.S. PATENT DOCUMENTS

| 5,279,795 A | | 1/1994 | Hughes et al. |
| 5,326,449 A | * | 7/1994 | Cunningham ......... 204/403.09 |
| 6,326,228 B1 | | 12/2001 | Hughes et al. |
| 6,895,805 B2 | * | 5/2005 | Hoagland .................. 73/31.06 |
| 2002/0092525 A1 | | 7/2002 | Rump et al. |

FOREIGN PATENT DOCUMENTS

| DE | 19854396 A | * | 6/2000 |
| DE | 10204458 A1 | | 8/2003 |
| EP | 0448052 A | | 9/1991 |
| FR | 2781054 A | | 1/2000 |

OTHER PUBLICATIONS

Hughes Robert C. et al., "Sensors for Detecting Molecular Hydrogen Based on Pd Metal Alloys", Sandia National Laboratories, Microsensor Research and Development Department, Albuquerque, NM, 1997.
W L Gore & Associates, "GORE™ Membrane Vents, Series HPM: High Protection Against Metal Impact" Product Data Sheet, 2002.

* cited by examiner

*Primary Examiner*—Daniel S. Larkin
(74) *Attorney, Agent, or Firm*—McAndrews, Held & Malloy, Ltd.

(57) ABSTRACT

A gas sensor assembly detects a constituent in a gaseous stream. The assembly comprises: (a) a mounting surface, (b) a sensor mounted on the mounting surface and sensor capable of generating a detectable signal in the presence of the constituent, and (c) an enclosing structure. The enclosing structure comprises: (i) a walled component having a pair of vertically spaced ends and mounted at one end on the mounting surface so as to circumscribe the sensor, and (ii) a gas-permeable membrane attached at the other end of the walled component, thereby defining an interior volume within said enclosing structure. Flowing the gaseous stream across the membrane infuses a portion of the gaseous stream into said interior volume containing the sensor.

17 Claims, 1 Drawing Sheet

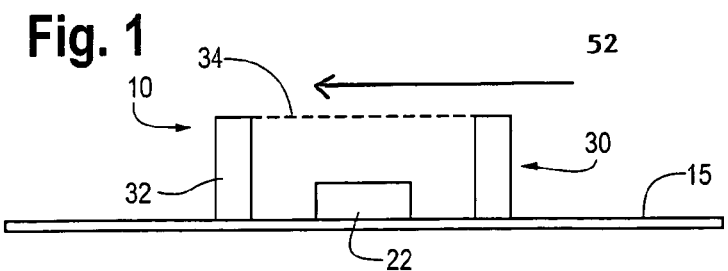
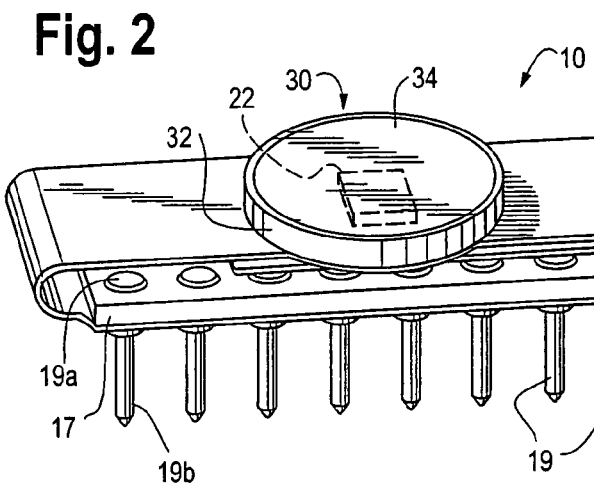
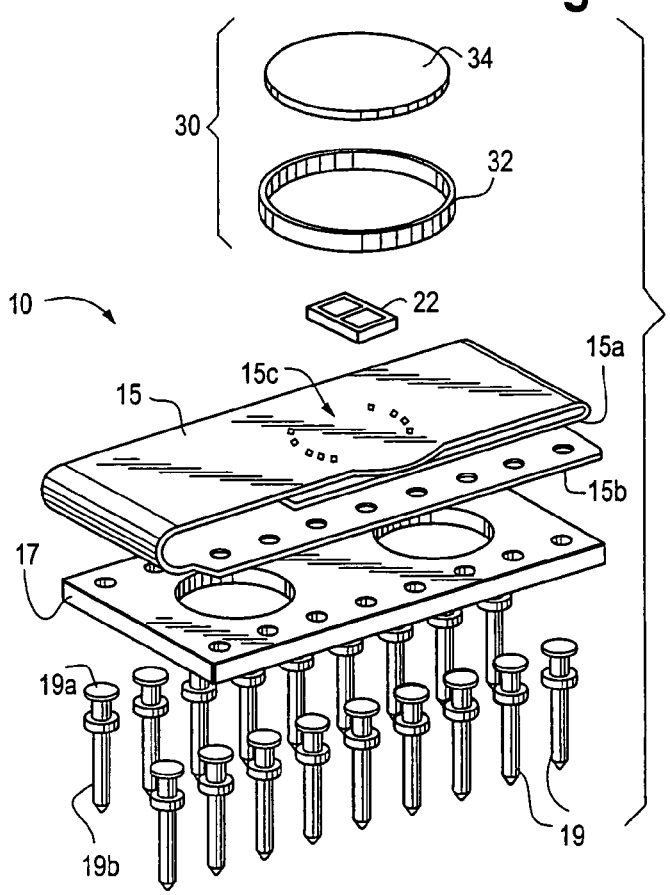

ISOLATED GAS SENSOR CONFIGURATION

CROSS-REFERENCE TO RELATED APPLICATION(S)

This application is related to and claims priority benefits from U.S. Provisional Patent Application Ser. No. 60/540,018, filed on Jan. 27, 2004. The '018 provisional application is hereby incorporated by reference herein in its entirety.

FIELD OF THE INVENTION

The present invention relates to sensors for detecting the presence of a constituent in a gaseous stream. More particularly, the present invention relates to a hydrogen gas sensor configuration in which the sensor is isolated within an enclosing structure that is interposed between a mounting surface and a gas-permeable membrane.

BACKGROUND OF THE INVENTION

In certain gas sensor applications, it is desirable to keep the sensor isolated from the external environment without impeding its functionality. Such isolation can be for the purpose of reducing or minimizing heat loss, reducing or minimizing the amount of light reaching the sensor, and/or reducing or minimizing the consequences of mechanical intrusion. Often, a sensor is operated at a given temperature, typically greater than that of the surrounding gas stream it is sensing. This is sometimes accomplished by the use of heat-producing devices disposed on the same substrate as the gas-sensing device. When this is the case, there is a finite amount of heat lost to the gas stream and structures surrounding the sensor. This heat loss is proportional to an amount of power loss from the entire system in which the sensor has been incorporated, and it is therefore desirable to reduce or minimize such heat loss. In addition, for some sensors it is desirable to limit the amount of light reaching the sensors. For most sensors, it is also desirable to limit mechanical or physical intrusion, either from particles entrained in the gas stream to be sensed or accidental occurrences such as the device being dropped.

Conventional, prior art thermal isolation techniques include fabricating the sensor itself in such a way as to create structures to provide thermal isolation (see, for example, U.S. Pat. Nos. 5,211,053, 5,464,966, 5,659,127, 5,883,009 and 6,202,467). Such exemplary thermal isolation techniques were designed specifically for the type of construction of the sensor involved and did not overcome the problems associated with heat loss at an assembly level, that is, where the sensor is configured as part of a greater assembly. Prior implementations of such gas-sensing devices, such as catalytically-based gas sensors, have employed different techniques to thermally isolate the device, such as suspending the device, within the gas stream being sensed, using individual wires that electrically connect the sensing device to its downstream processing and control circuitry (see, for example, U.S. Pat. No. 5,902,556), but these methods are not preferred for a sensor with multiple connections.

The foregoing prior art solutions have the disadvantage of being considerably more voluminous and bulky than is desirable for most end-uses. Additionally, design parameters of the prior art sensors have trade-offs, such as response-to-size and isolation-to-flow effects. "Response-to-size" refers to the relationship between the magnitude of the isolated gas volume exposed to a sensor and the amount of time for a complete exchange of the gaseous constituents within the isolated volume; the smaller the size of the isolated gas volume, the more rapid a complete exchange will occur. "Isolation-to-flow" refers to the relationship between the flow rate of a gas stream exposed to a sensor and the magnitude and rate of heat loss from the sensor; higher gas stream flow rates draw greater amounts of heat from a sensor more rapidly, thereby increasing power consumption by the sensor in order to restore lost heat. Moreover, such prior art solutions did not address the optical sensitivity of certain sensors. In this regard, capacitor-based devices are generally sensitive to light and can generate erroneous, stray signals upon exposure to light.

SUMMARY OF THE INVENTION

The present gas sensor assembly having a configuration in which the sensor is isolated overcomes one or more of the foregoing shortcomings of prior art gas sensors. In particular, the present isolated gas sensor configuration reduces power consumption, limits the unfavorable effects of ambient light, and limits mechanical intrusion through the use of a geometry that provides a gas-filled gap and an enclosing structure that includes a gas-permeable membrane.

In one embodiment, the present gas sensor assembly for detecting a constituent in a gaseous stream comprises:

(a) a mounting surface;

(b) a sensor mounted on the mounting surface, the sensor capable of generating a detectable signal in the presence of the constituent and;

(c) an enclosing structure comprising:
  (i) a walled component having a pair of vertically spaced ends, the walled component mounted at one end on the mounting surface and circumscribing the sensor; and
  (ii) a gas-permeable membrane attached at the other end of the walled component, thereby defining an interior volume within the enclosing structure.

Flowing the gaseous stream across the gas-permeable membrane infuses a portion of the gaseous stream into the interior volume containing the sensor.

In a preferred embodiment of the present gas sensor assembly, the gas-permeable membrane has optical properties that inhibit passage of light into the interior volume. The gas-permeable membrane is non-transparent and, more preferably, opaque.

The gas-permeable membrane is preferably and, more preferably, a polytetrafluoroethylene-based membrane material.

In a preferred embodiment of the present gas sensor assembly, the mounting surface is formed on a flexible circuit and the mounting surface is planar.

In an illustrative embodiment of the present gas sensor assembly, the sensor is sensitive to hydrogen and is catalytically activated.

In a preferred embodiment of the present gas sensor assembly, the walled component is tubular and is formed from a polymeric electrically insulative material, preferably an acetal resin.

A method of isolating, in a gas sensor assembly, a sensor capable of generating a detectable signal in the presence of a gas stream constituent, comprises:

(a) mounting the sensor on a mounting surface and;

(b) enclosing the sensor in an enclosing structure comprising:

(i) a walled component having a pair of vertically spaced ends, the walled component mounted at one end on the mounting surface and circumscribing the sensor; and (ii) a gas-permeable membrane attached at the other end of the walled component, thereby defining an interior volume within the enclosing structure;:

Flowing the gaseous stream across the gas-permeable membrane infuses a portion of the gaseous stream into the interior volume containing the sensor.

In a preferred embodiment of the isolating method, the gas-permeable membrane has optical properties that inhibit the passage of light into the interior volume, and the gas-permeable membrane is preferably non-transparent.

A method of detecting a constituent in a gaseous stream, the method comprises:

(a) mounting a sensor on a mounting surface, the sensor capable of generating a detectable signal in the presence of the constituent;

(b) enclosing the sensor in an enclosing structure comprising:
  (i) a walled component having a pair of vertically spaced ends, the walled component mounted at one end on the mounting surface and circumscribing the sensor; and
  (ii) a gas-permeable membrane attached at the other end of the walled component, thereby defining an interior volume within the enclosing structure;

(d) flowing the gaseous stream across the gas-permeable membrane whereby a portion of the gaseous stream infuses into the interior volume and the impinges upon the sensor; and (e) generating a detectable signal from the sensor in the presence of the constituent.

In a preferred embodiment of the isolating method, the gas-permeable membrane has optical properties that inhibit the passage of light into the interior volume, and the gas-permeable membrane is preferably non-transparent.

BRIEF DESCRIPTION OF THE DRAWING(S)

FIG. 1 is a schematic diagram showing a cross-sectional view of a first basic configuration of the present isolated gas sensor assembly.

FIG. 2 is a perspective view of one embodiment of a gas sensor assembly that implements the configuration illustrated schematically in FIG. 1.

FIG. 3 is an exploded perspective view of the gas sensor assembly of FIG. 2.

DETAILED DESCRIPTION OF PREFERRED EMBODIMENT(S)

A first basic configuration of the present isolated gas sensor assembly 10 is shown schematically in FIG. 1. Gas sensor assembly 10 includes a flexible circuit surface 15 upon which are mounted a sensor 22, an enclosing structure 30 that includes a walled component 32, and a gas-permeable membrane 34, as depicted. An interior volume or gas-filled gap is formed within enclosing structure 30, bounded on the bottom by flex circuit 15 and sensor 22, bounded on the side by the walls of component 32, and bounded on the top by membrane 34.

In the depicted assembly, flex circuit surface 15 has a flexible (and foldable) planar surface on which sensor 22 and enclosing structure 30 can be securely mounted.

The mounting surface could conceivably assume surface configurations other than planar depending upon the application in which the gas sensor configuration is to be incorporated. Such mounting surface configurations could include, for example, arcuate or spheroidal configurations in which the surface on which the sensor and enclosing structure are mounted are non-planar.

Sensor 22 is capable of generating a detectable signal in the presence of the gaseous constituent to be detected, which is hydrogen in the embodiments illustrated herein. The electrical signal generated by sensor 22 is conducted via copper traces (not shown) formed in the flex circuit and transmitted to downstream electrical signal processing and control circuitry that transforms the signal to a perceivable output that is indicative of the presence and concentration of the gas stream constituent to be detected (hydrogen in the illustrated embodiment).

In the case of the hydrogen gas sensor specifically described herein, the sensor generates a signal derived from the catalytic reaction of the sensor components or elements with hydrogen that is present in the gas stream to be assessed. Suitable hydrogen sensor configurations include wide range sensors developed at Sandia National Laboratories (see R. Thomas and R. Hughes, "Sensors for Detecting Molecular Hydrogen Based on PD Metal Alloys", *J. Electrochem. Soc.*, Vol. 144, No. 9, September 1997; and U.S. Pat. No. 5,279,795), as well as the integrated sensor configurations developed by H2Scan LLC and described in applications filed concurrently herewith.

Reducing or minimizing the heat loss through convective currents is enabled or facilitated by the cooperation of gas-permeable membrane 34 with walled component 32 and flex circuit surface 15 to enclose gas sensor 22 within enclosing structure 30. Since the function of a gas sensor is to detect and measure the specific concentration of gaseous constituent(s) in a given atmosphere, gas sensor assembly 22 is necessarily exposed to some larger volume of a flowing gas stream (not shown). This gas stream can be subjected to currents that are either natural in occurrence or induced by the flow of the gas stream through a conduit (not shown). The isolation of sensor 22 from these currents by use of the surrounding enclosing structure 30, including gas-permeable membrane 34, provides a further reduction in power loss from sensor 22.

Gas-permeable membrane 34 allows the gas being sensed to reach the sensor 22 for the purpose of measurement, but membrane 34 also limits the velocity at which the gas stream 52 being measured flows past sensor 22. Since the convective heat loss from a surface is a function of the fluid velocity of the impinging gas stream, the heat loss from sensor 22 is thereby limited to a reduced amount by its location within enclosing structure 30.

As depicted in FIG. 1, gas-permeable membrane 34 is attached at the upper end of the enclosing structure (that is, the end opposite that mounted on the mounting surface) so as to define an interior volume within the enclosing structure that is isolated from the external environment.

FIGS. 2 and 3 illustrate an embodiment of the present isolated gas sensor configuration in assembled form (FIG. 2) and in exploded form (FIG. 3). As shown in FIGS. 2 and 3, gas sensor assembly 10 includes a flex circuit surface 15 on which are mounted a sensor 22, an enclosing structure 30 that includes a walled component 32, and a gas-permeable membrane 34. An interior volume or gas-filled gap is formed within enclosing structure 30, bounded on the bottom by flex circuit 15 and sensor 22, bounded on the side by the walls of component 32, and bounded on the top by membrane 34.

As shown in FIG. 2 and better shown in FIG. 3, sensor 22 is mounted at a central portion 15c along the longitudinal extent of flex circuit 15. End portion 15a of flex circuit 15 is folded under central portion 15c to create a structure in which folded-under end portion 15a supports central portion 15c and prevents central portion 15c from contacting the underlying components of assembly 10. The support afforded by folded-under end portion 15a also enables a gap or volume to be maintained under central portion 15c and sensor 22 mounted thereon, thus thermally isolating sensor 22 from the underlying components of assembly 10.

As further shown in FIGS. 2 and 3, flex circuit 15 terminates in an end portion 15b, in which the copper traces (not shown) that extend from sensor 22 are electrically connected to pin connectors 19. Each pin connector has a head portion 19a and a spiked portion 19b. In the illustrated embodiment, a copper trace extending from gas sensor 22 is electrically connected to pin connector head 19a. The spiked portions of pin connectors 19 are inserted through holes in end portion 15b of flex circuit 15, then through aligned holes in an electrically insulative support layer 17. The spiked portions of pin connectors 19 are insertable into aligned mounting holes in a circuit board (not shown), which contains the downstream processing and control circuitry to which the signals from sensor 22 are directed.

The gas-permeable membrane preferably has optical properties that inhibit the passage of light into the interior volume of the enclosing structure. The preferred gas-permeable membrane is non-transparent (preferably opaque), and is formed from a polymeric material. A suitable gas-permeable membrane material is a polytetrafluoroethylene-based membrane material commercially available from W.L. Gore & Associates under the trade name Gore™ Membrane Vents (available in various vent diameter and airflow grades under Part Nos. VE70308, VE70510, VE70814, VE70919, VE71221 and VE72029). Other suitable non-polymeric gas-permeable membrane materials could be employed as well, such as, for example, porous metallic membranes.

In addition to reducing heat loss, the optical isolation of certain gas sensors is desirable to reduce or minimize interference from light with signals representing the gas constituent(s) being measured. The use of certain gas-permeable membranes can reduce or minimize the intrusion of ambient light upon gas sensor 22. Enclosing structure 30 is therefore preferably fabricated from an opaque material so that, in conjunction with membrane 34, sensor 22 is kept in a light-controlled environment.

The use of a gas-permeable membrane and structural elements enclosing the sensor reduces or minimizes the potential for mechanical intrusion. Intrusion could take the form of particles entrained in the gas being sensed instead of the gas constituent to be detected. Such intrusions could also take the form of accidental occurrences, such as the gas sensor assembly, or the overall system in which it is integrated, being dropped or prodded. The protection afforded by the enclosing structure reduces or minimizes the chance of damage to the sensor and its connections to related components.

Conventional, prior art solutions employed sintered metal disks primarily to reduce flow sensitivity and to prevent mechanical intrusion. These prior solutions have disadvantages in relation to the present gas sensor assembly, namely;
prior art gas sensors are significantly greater in volume than the present solution;
prior art gas sensors do not isolate the gas stream in which the constituent(s) to be tested are flowed;
prior art gas sensors form much larger isolated volumes: and
prior art gas sensors do not inhibit light from entering the isolated volume.

In the prior designs, trade-offs were made among the porosity of the sintered metal, its thickness, and the isolated volume. If the porosity of the sintered metal were too great (that is, having a prevalence of open pores in its interior volume) or if the sintered metal disk were too thin, the effects of flow rate were more pronounced. In this regard, low porosity of the sintered metal disk reduces response time (that is, the difference between the time a change occurs in the concentration of the gas constituent being detected and the time the gas sensor and its associated processing and control circuitry register the change). Although such sintered metal disks are generally able to block most of the light to which the sensor is exposed, the degree of blockage is generally inadequate for sensors that are sensitive to low-level light. Sensor assembly designs that employ these sintered metal isolating disks must therefore accept trade-offs between competing performance variables. The present design is essentially independent of such design trade-offs, since the performance variables improve with reduced size of the gas sensor assembly.

In the present gas sensor assembly, the gas-permeable membrane is held in position by walled component of the enclosing structure, which could be as simple as a ring formed of electrically insulative material, such as, for example, a ring formed from an acetal resin (commercially available from DuPont under the trade name Delrin®). The enclosing structure could also be formed in shapes, other than a ring, yet having a hollow interior volume to accommodate the sensor. The gas-permeable membrane is preferably placed directly over the sensor and preferably also encloses the wire extending between the sensor and the processor and/or other elements that make up the overall sensor assembly. The resulting structure accommodates the use a relatively small volume of an isolated gas stream, which improves sensor response.

The isolated gas stream in the volume of the enclosing structure of the present gas sensor assembly also has convection properties that are reduced in relation to those of prior art sensors, in which the sensor is exposed to the sample gas volume, thereby reducing power loss in the present design. The performance of the present sensor assembly is substantially unaffected by flow in the sample gas volume, since it is mechanically isolated from the sample gas volume. The barriers of the enclosing structure and gas-permeable membrane in the present gas sensor assembly also protect the sensor from various forms of intrusion and contamination, such as from mechanical impact, droplets of liquid contaminants, dust, and the like. Finally, the preferred membrane in the present gas assembly is opaque to ambient light and isolates light-sensitive sensors from the external environment.

The advantages of the present isolated gas sensor configuration include the isolation of the sensor from: light, sample gas stream flow, mechanical intrusion (handling, dust, and the like), and liquid contaminant intrusion, without substantially compromising sensor response while providing thermal isolation.

While particular steps, elements, embodiments and applications of the present invention have been shown and described, it will be understood, of course, that the invention is not limited thereto since modifications can be made by those skilled in the art, particularly in light of the foregoing teachings.

What is claimed is:

1. A gas sensor assembly for detecting a constituent in a gaseous stream, the assembly comprising:
    (a) a mounting surface;

(b) a sensor mounted on the mounting surface, said sensor capable of generating a detectable signal in the presence of said constituent; and
(c) an enclosing structure comprising:
  (i) a walled component having a pair of vertically spaced ends, the walled component mounted at one end on said mounting surface and circumscribing said sensor; and
  (ii) a gas-permeable membrane attached at the other end of said walled component, thereby defining an interior volume within said enclosing structure, said gas-permeable membrane having optical properties that inhibit passage of light into said interior volume;
whereby flowing the gaseous stream across said gas-permeable membrane infuses a portion of the gaseous stream into said interior volume containing said sensor, wherein said mounting surface is formed on a flexible circuit, said flexible circuit having a central portion and two end portions, at least one of said end portions capable of being folded under said central portion such that said central portion does not contact underlying components of said sensor assembly.

2. The gas sensor assembly of claim 1 wherein said gas-permeable membrane is non-transparent.

3. The gas sensor assembly of claim 2 wherein said gas-permeable membrane is opaque.

4. The gas sensor assembly of claim 1 wherein said gas-permeable membrane is polymeric.

5. The gas sensor assembly of claim 1 wherein the gas-permeable membrane is a polytetrafluoroethylene-based membrane material.

6. The gas sensor assembly of claim 1 wherein said mounting surface is planar.

7. The gas sensor assembly of claim 1 wherein said sensor is sensitive to hydrogen.

8. The gas sensor assembly of claim 7 wherein said sensor is catalytically activated.

9. The gas sensor assembly of claim 1 wherein said walled component is tubular.

10. The gas sensor assembly of claim 1 wherein said walled component is formed from an electrically insulative material.

11. The gas sensor assembly of claim 10 wherein the electrically insulative material is polymeric.

12. The gas sensor assembly of claim 11 wherein the electrically insulative material is an acetal resin.

13. The gas sensor assembly of claim 1 wherein said at least one folded end portion forms a gap, said gap thermally isolating said sensor from said sensor assembly underlying components.

14. A method of isolating, in a gas sensor assembly, a sensor capable of generating a detectable signal in the presence of a gas stream constituent, the method comprising:
  (a) mounting said sensor on a mounting surface and;
  (b) enclosing said sensor in an enclosing structure comprising:
    (i) a walled component having a pair of vertically spaced ends, the walled component mounted at one end on said mounting surface and circumscribing said sensor; and
    (ii) a gas-permeable membrane attached at the other end of said walled component, thereby defining an interior volume within said enclosing structure, said gas-permeable membrane having optical properties that inhibit passage of light into said interior volume;
whereby flowing the gaseous stream across said gas-permeable membrane infuses a portion of the gaseous stream into said interior volume containing said sensor, wherein said mounting surface is formed on a flexible circuit, said flexible circuit having a central portion and two end portions, at least one of said end portions capable of being folded under said central portion such that said central portion does not contact underlying components of said sensor assembly.

15. The method of claim 14 wherein said gas-permeable membrane is non-transparent.

16. A method of detecting a constituent in a gaseous stream, the method comprising:
  (a) mounting a sensor on a mounting surface, said sensor capable of generating a detectable signal in the presence of said constituent;
  (b) enclosing said sensor in an enclosing structure comprising:
    (i) a walled component having a pair of vertically spaced ends, the walled component mounted at one end on said mounting surface and circumscribing said sensor, wherein said mounting surface is formed on a flexible circuit, said flexible circuit having a central portion and two end portions, at least one of said end portions capable of being folded under said central portion such that said central portion does not contact underlying components of said sensor assembly; and
    (ii) a gas-permeable membrane attached at the other end of said walled component, thereby defining an interior volume within said enclosing structure, wherein said gas-permeable membrane has optical properties that inhibit the passage of light into said interior volume;
  (d) flowing the gaseous stream across said gas-permeable membrane whereby a portion of said gaseous stream infuses into said interior volume and the impinges upon said sensor; and
  (e) generating a detectable signal from said sensor in the presence of said constituent.

17. The method of claim 16 wherein said gas-permeable membrane is non-transparent.

* * * * *